United States Patent [19]
Epstein et al.

[11] 4,008,521
[45] Feb. 22, 1977

[54] DENTAL TOOLS

[75] Inventors: Arthur M. Epstein; Hans E. Baumayr, both of New York, N.Y.

[73] Assignee: Baumayr Instrument Co., Inc., New York, N.Y.

[22] Filed: Mar. 24, 1976

[21] Appl. No.: 670,026

Related U.S. Application Data

[63] Continuation-in-part of Ser. No. 496,786, Aug. 12, 1974, abandoned.

[52] U.S. Cl. .................................................. 32/27
[51] Int. Cl.² ............................................. A61C 1/10
[58] Field of Search ............. 32/52, 53, 54, 55, 27, 32/26

[56] References Cited
UNITED STATES PATENTS

| | | | |
|---|---|---|---|
| 170,342 | 11/1875 | Buckingham et al. | 32/53 |
| 597,469 | 1/1898 | Marshall | 32/54 |

*Primary Examiner*—Robert Peshock
*Attorney, Agent, or Firm*—Wolder & Gross

[57] ABSTRACT

A dental tool includes an articulated tubular body member having proximal and distal sections angularly adjustable about an elbow housing. An axial drive shaft is located in the proximal section and a slide member is reciprocable in the distal section and spring urged to a retracted position and coupled to the drive shaft by a rotary to reciprocatory motion translator. The motion translator includes an actuator located in the elbow section and limited to a rocking motion and rotatably engaging an eccentric projection forwardly from the shaft at an angle thereto and a connecting rod having spherical ends which respectively engage a mating gripping socket in the actuator eccentric to the pin and a mating gripping socket at the rear of the slide member. A tool holding chuck is carried by the distal end of the slide member. In a modified form the retractor spring is omitted and the connecting rod is coupled to the slide member by a rack and pinion. The reciprocating stroke of the slide member is insignificantly affected by its angle to the drive shaft.

14 Claims, 9 Drawing Figures

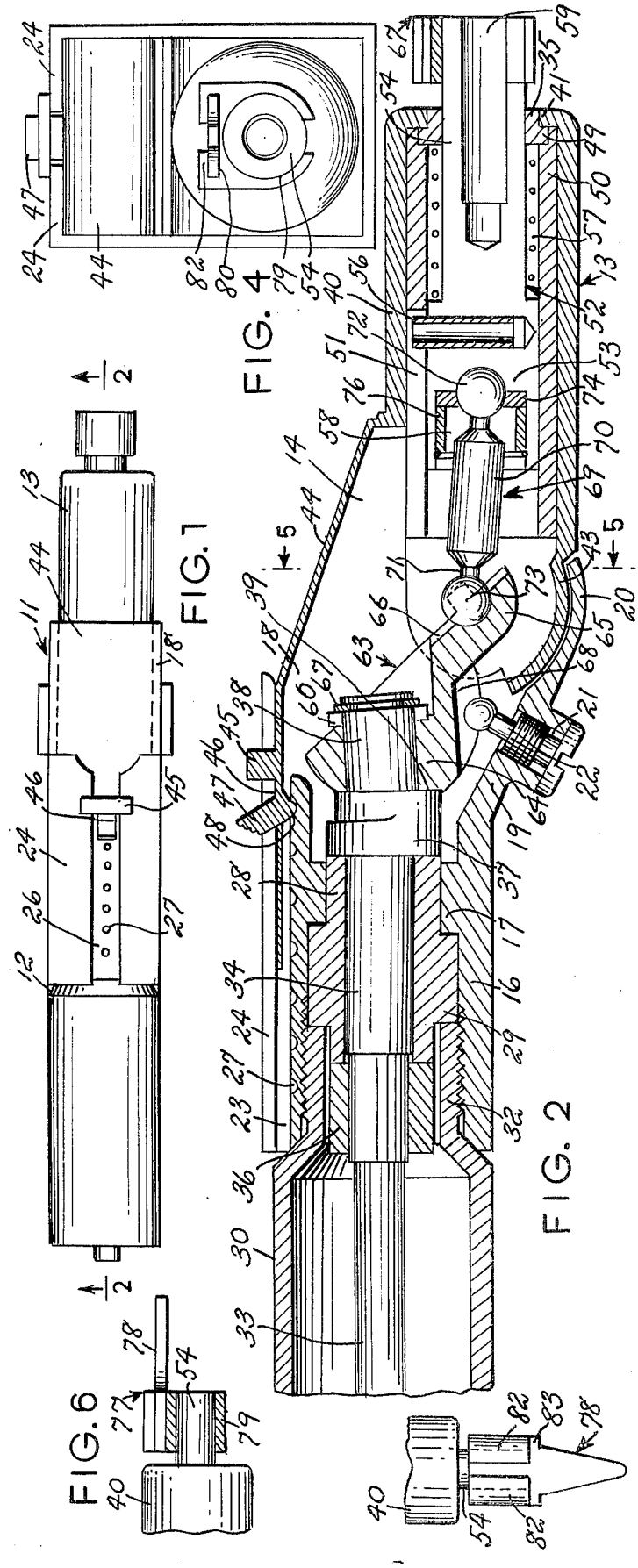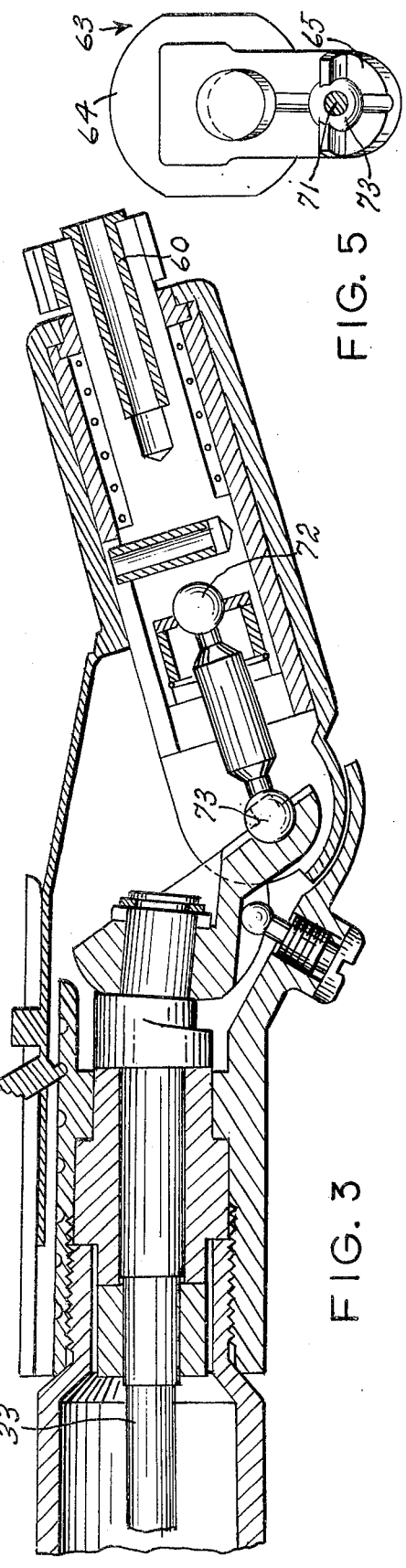

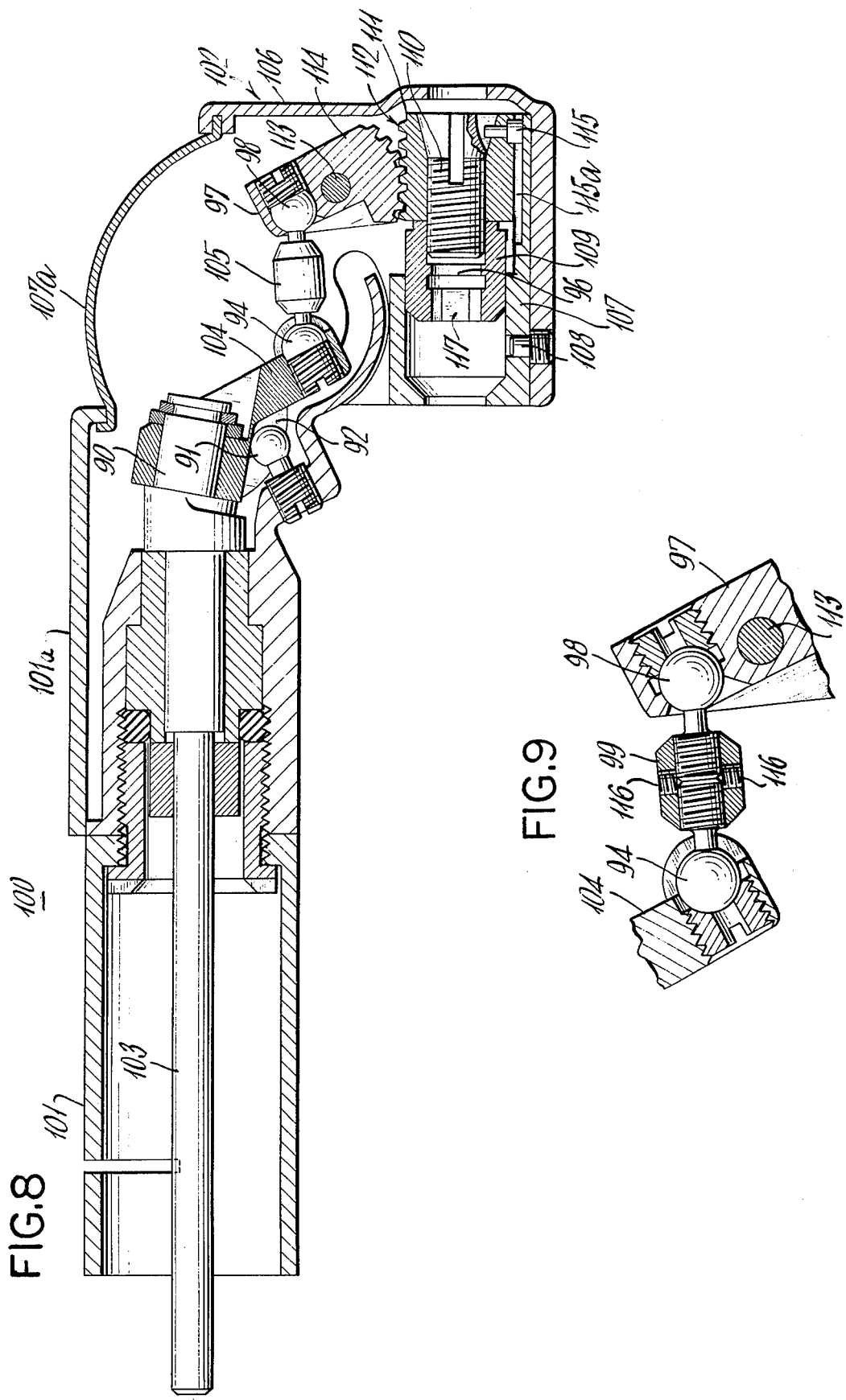

DENTAL TOOLS

REFERENCE TO RELATED APPLICATION

The present application is a continuation-in-part of patent application Ser. No. 496,786 filed Aug. 12, 1974 and now abandoned.

BACKGROUND OF THE INVENTION

The present invention relates generally to dental tools, and it relates more particularly to a multi-angle reciprocating dental tool which may be used under the gingivae and on those portions of the teeth now inaccessible to rotary tools.

One of the long existing problems in the field of dental technology has been the difficulty in developing a tool which can provide a reciprocal motion and which can properly and successfully reach under the gingivae and those areas of the tooth which are now inaccessible to present lineal and rotary motion tools.

The previous attempts to resolve this problem have resulted in tools which move in arcs, which rock, and which describe a reciprocal motion but only in a single direction. The end result of these earlier tools was that gums were often pounded, and the teeth were also battered, resulting in trauma.

Many of the reciprocating tools were also improperly designed so that the work load created at the end of the tool was greater than the design limitations of the tool, and it would either stop its motion, or would work improperly.

Other prior art design tools would continue their movement, but the tool itself would be stationary and the body of the tool would move when placed against the work area. It is accordingly clear that the dental tools heretofore available leave much to be desired.

SUMMARY OF THE INVENTION

It is a principal object of the present invention to provide an improved dental tool which will provide a reciprocal and lineal cycle.

Another object of the present invention is to provide an improved reciprocating tool which follows a sine wave pattern.

Still another object of the present invention is to provide a device of the character described which because of its sine wave pattern will dwell at the extremities of its reciprocal movement, thus eliminating pounding of the tooth or pulp.

Still another object of the present invention is to provide a device of the character described which may be easily adjustable through a 90° arc thus greatly adding to the utility of the tool.

Still another object of the present invention is the simple replacement of the tooth and pulp engaging portion of the tool and the adaptability of the tool itself to receive a variety of such members.

Still another object of the present invention is to provide a multi-angle reciprocating dental tool which will be simple and inexpensive to manufacture and assemble, and yet be durable to a high degree in use.

The above and other objects of the present invention will become apparent from a reading of the following description taken in conjunction with the accompany drawings which illustrate a preferred embodiment thereof.

In a sense the present invention contemplates the provision of a dental tool comprising an articulated member including a pair of angularly adjustable proximal and distal tubular sections, a longitudinally extending shaft journalled in the proximal section, a slide member longitudinally reciprocable in the distal section, a tool holder located on the front end of the slide member and a rotation to reciprocation motion translator coupling the shaft to the slide member and effective to reciprocate the slide member at a stroke which is substantially independent of the angular relationship between the proximal and distal sections for a wide range of such angular relationship.

In the preferred form of the improved dental tool, the motion translator includes an actuator journal projecting forwardly from the drive shaft at a small angle to the axis thereof, for example, about 10°. An actuator member is located in the elbow area between the proximal and distal sections and is rockable about a transverse axis and restricted against rotation about the axis of the shaft. The actutor member includes a first arm having a bore engaging the actuating pin so that rotation of the shaft rocks the actuating member and a forwardly, outwardly inclined second arm having a spherically surfaced first gripping socket in its front face. The slide member has a spherically surfaced second gripping socket in its rear face and a connecting rod is provided at opposite ends with balls which engage the corresponding sockets for universal rotation therein. A finger actuated latch is provided for releasably locking the proximal and distal sections in adjusted angular positions. Other designs, such as spring loaded pusher members, may be utilized. In a modified form of the device which is adapted for use in confined spaces, the connecting rod is coupled to the slide member by a rack and pinion transmission.

The improved device is highly reliable, rugged and inexpensive, compact and of great versatility and adaptability. The reciprocating stroke of the tool holding shank is sinusoidal and of a substantially constant length, whose variation with the angular adjustment between the axis of the drive shaft and reciprocating slide member is insignificant.

BRIEF DESCRIPTION OF THE DRAWINGS

FIG. 1 is a top plan of a dental tool device embodying the present invention;

FIG. 2 is a medial longitudinal sectional view taken along line 2—2 in FIG. 1;

FIG. 3 is a view similar to FIG. 2 showing the device in an angularly adjusted position;

FIG. 4 is a front elevational end view thereof;

FIG. 5 is a sectional view taken along line 5—5 in FIG. 2;

FIG. 6 is a longitudinal medial sectional view of the tool coupling chuck mounted on the tool device;

FIG. 7 is a top plan view thereof;

FIG. 8 is a view similar to FIG. 2 of another embodiment of the present invention; and FIG. 9 is an enlarged detailed view of a section thereof.

DESCRIPTION OF THE PREFERRED EMBODIMENTS

Referring now to the drawings, particularly FIGS. 1 to 7 thereof which illustrate a preferred embodiment of the present invention, the reference numeral 10 generally designates the improved dental tool device which is mountable to the end of a handpiece provided with a motor driven shaft or air turbine coupling in the known manner having at an end thereof a suitable drive coupling which drive engages the drive shaft of the device 10 merely by attaching the device to the handpiece. The device 10 comprises an articulated tubular body 11 including a proximal tubular section 12 and a distal tubular section 13 transversely offset from section 12 and connected thereto for angular adjustment about a transverse axis at an elbow portion 13 by suitable transversely aligned pivot pins at opposite sides of the elbow portion 14.

The proximal section 12 includes a front sleeve 16 of rectangular external transverse cross section and having a circular axial bore therein whose rear portion is threaded and which is provided proximate its forward portion with a peripheral inwardly projecting rib 17 having forwardly facing shoulder. Projecting rearwardly from the opposite side faces of sleeve 16 are a pair of transversely spaced parallel similar side arm plates 18, the bottom edges of which are joined by an integrally formed inclined cross web 19 having a cylindrical front portion 20 coaxial with the transverse pivotal axis of the body member sections. Medially formed in web 19 rearwardly of portion 20 is a forwardly, upwardly inclined tapped bore 21 surrounded by an outwardly projecting collar and engaged by the enlarged threaded section of a pivot guide pin 22 having a spherical tip located within elbow portion 14. The outer end of pin 22 is provided with an enlarged head engaging the end face of the bore surrounding collar.

Projecting upwardly from the side faces of sleeve 16 are longitudinally extending flanges which terminate in inwardly directed coplanar horizontal walls 24 which project forwardly of sleeve 16. Walls 24 have transversely spaced confronting parallel edges delineating a longitudinal guide slot 26 and are spaced above the top faces of sleeve 16. A group of longitudinally spaced recesses 27 are formed in the top face of sleeve 16 and are medially aligned with the slot 26.

Coaxially nested in the bore of sleeve 16 is an axially extending bearing bushing 28 having between its ends an enlarged peripheral section 29 having a front shoulder bearing on the rear shoulder of rib 17 and a rearwardly facing shoulder. A rear coupling sleeve 30 includes an externally threaded reduced diameter front section 32 which engages the threaded rear bore of sleeve 16, and tightly bears on the rear shoulder of bushing portion 29 to securely lock the bushing in the bore of sleeve 16. The front portion of bushing 28 projects forwardly of rib 17 and the rear portion thereof projects into sleeve front section 32.

A drive shaft 33 is coaxial with and extends along proximal tubular section 12 and includes an enlarged cylindrical portion 34 proximate its forward part rotatably journalled in the bushing 28. A collar 36 is affixed to shaft 33 immediately rearwardly of shaft enlarged portion 34 and abuts the rear face of bushing 28 to prevent the forward axial movement of shaft 33 and the shaft enlarged section 34 terminates at its front end in an enlarged head 37 having a transverse rear peripheral shoulder abutting the front face of bushing 28 to prevent the rearward axial movement of shaft 33.

Rotatable with shaft 33 and projecting forwardly from the head 37 is an actuator pin 38 whose longitudinal axis is at an obtuse angle to the longitudinal axis of shaft 33. The diameter of actuator pin 38 is approximately equal to that of enlarged section 34 and center of the base of actuator pin 38 is transversely offset from the axis of shaft 33 and lies in the plane of the front face 39 of head 37 which is perpendicular to the axis of actuator pin 38.

The distal tubular section 13 includes a tubular outer shell 40 transversely offset from sleeve 16 and terminating at its front end in an inwardly directed peripheral flange 41. Extending rearwardly from the lower rear edge of shell 40 is an elongated resilient tongue 43 which slideably engages the cylindrical inside face of the sleeve front portion 20. A resilient flexible strip 44 is integrally formed with and extends rearwardly from the top rear wall of shell 40 into sliding engagement with the underfaces of guide walls 24 and the inside faces of flanges 23. The strip 44 terminates at its rear in a medial narrow tongue 46. A vertical releasable lock defining finger piece 47 is formed at the end of tongue 46 and projects upwardly through slot 26 and is provided with a depending detent element 48 which is movable with strip 44 into releasable engagement with a selected recess 27 whereby to releasably lock the shell 40 into an adjusted angular relationship with the section 12. In order to facilitate the body member angular adjustment a knob 45 is connected by an integrally formed shank with the strip 44 immediately forwardly of lock member 47 and slideably engages the top faces of guide walls 24.

A bushing 35 engages the front opening in shell 40 and has a peripheral flange 49 at its rear border which bears on the rear face of shell flange 41. A low friction sleeve 50 tightly telescopes the shell 40 and has a stepped front face abutting the rear outer peripheral corner of bushing 35 and extends for the full length of shell 40. A longitudinal slot 51 is formed in the rear upper part of sleeve 50.

Reciprocatably coaxially disposed in sleeve 50 is a piston or slide member 52 including an enlarged rear cylindrical portion 53 whose outside face slideably engages the inside face of sleeve 50 and a front cylindrical shank portion 54 of reduced diameter which slideably engages the bushing 35. A radial bore is formed in the piston enlarged section 53 and is engaged by a tubular pin 56 which projects into sliding engagement with slot 51 to prevent rotation of the piston 52. A helical compression spring 57 encircles shank section 54 and entrapped between the shoulder delineating piston sections 53 and 54, and the rear face of bushing 35 to rearwardly bias the piston 52 toward its retracted position. A cylindrical well 58 is coaxially formed in the rear face of piston section 53 and has centrally formed in the front face or base thereof, a hemispherical socket. A tapped axial bore is formed in the front section of shank 54 for releasably receiving and retaining a tubular polymeric resin chuck 60 provided with a front peripheral flange engaging the front face of shank 54.

An integrally formed actuator member 63 is rockably disposed in the elbow section 14 and includes a rear transverse section or arm 64 and a forwardly, outwardly inclined front section or arm 65 having a forwardly, directed face 66. The actuator arm 64 has a bore formed therein which rotatably engages actuator pin 38 projecting through the bore, the arm 64 being restricted against axial movement on pin 38 by an annulus 60, bearing on the front face of arm 64 and locked in position by a ring 67 engaging a groove in pin 38 and abutting the front face of arm 64. The front and rear faces of arm 64 are parallel, the rear face engaging the front face of angularly displaced spherical shoulder of enlarged head 37.

A longitudinal groove 68 is formed in the outer face of the knee between arms 64 and 65 and is slideably engaged by the end portion of pin 22. The actuator member 63 is thus prevented from rotation about the longitudinal axis and is rocked about a transverse axis by the rotation of shaft 33. A spherically faced socket is formed in the front face of arm 65 proximate its outer end.

A coupling link drive connects actuator arm 65 and slide member 52 and includes a rod 70 provided at opposite ends with reduced diameter coaxial sections 71 which terminate in front and rear ball elements 72 and 73 respectively. The rear ball element 73 universally rotatably engages the spherical gripping socket in actuator arm 65 and is retained therein by suitably formed ears on arm 65 and the front ball element 72 universally rotatably engages the spherical gripping socket in the base of the sliding member well 58 and is retained therein by an annulus 74 engaging the rear peripheral face of ball element 72 and locked in position by a sleeve 76 telescoping the well 58 and bearing on the rear face of annulus 74 or other suitable means.

A chuck 77 for replaceably holding a tool 78 is mounted on the free front end of the slide member shank 54. The chuck 77 includes a yoke section defined by a pair of arcuate arms 79 defining a longitudinal bore and tightly embracing shank 54 and joined at their inner ends by a cross member 80. A pair of shallow parallel longitudinal side walls 81 project upwardly from the side edges of cross member 80 and terminate in inwardly directed coplanar flanges 82 which delineate with the top face of cross member 80 a channel for replaceably receiving and retaining the correspondingly shaped shank 83 of a tool 78. The tool 78 may be of any desired configuration and function, and may advantageously be an abrasive tool having abrasive faces of any desired roughness. The tools may be of the reusable or of a disposable type, and may be packaged for selection and dispensing in any suitable manner.

The device 10, in use, is separably mounted to the distal portion of a handpiece of conventional construction provided with a power driven rotating shaft terminating in a coupling element which engages the distal end of shaft 33 to controllably rotate the shaft 33. The rotation of shaft 33 effects the eccentric rotation of actuator pin 38 which is an integral part of shaft 33 and which in turn rocks or oscillates the actuator member 63 to thereby reciprocate the slide member 52 by way of link 70 and the tool-holding chuck 67. The angle between the axis of shaft 33 and the longitudinal axis of slide member 52 may be adjusted by retracting detent element 47 from a respective recess 27 by swinging finger piece 47 and advancing it to swing the distal section 13 to the desired angular position relative to the proximal section 12 and the detent 48 is released into locking engagement with a corresponding recess 27.

With the rotation of shaft 33 the slide member 52 linearly reciprocates at a velocity which varies in a sine manner with time independently of the angle between the axes of shaft 33 and slide member 52. Moreover, the reciprocating stroke of the slide member 52 is substantially constant and its variation with the angle between the axes of drive shaft 33 and drive member 52 is unsignificant for the full range of adjustment between sections 12 and 13. According to a preferred construction the angle between the axes of shaft 33 and actuator pin 38 is 10° and between the center of ball 73 and the plane perpendicular to the axis of pin 38 is 37.5°.

In FIGS. 8 and 9 of the drawings there is illustrated another embodiment of the present invention which differs from that first described embodiment primarily in the structure of the distal housing and piston or slide member and the mechanism coupling the motion translator to the piston to provide a modified tool 100 which is highly suitable for application in confined spaces. Specifically the modified device 100 includes a proximal section 101 similar in construction to the proximal section of the first embodiment and an angularly adjustable distal section 102. The proximal section 101 includes an elongated tubular housing in which a coaxial drive shaft 103 is suitably journalled. The shaft 103 upon rotation rocks an actuator member 104 about a transverse axis between the proximal and distal sections by means of a shaft carried axially inclined eccentric pin 90, the actuator member 104 being restricted to such rocking motion by a stationary guide element 91 engaging a guide groove 92 in actuator member 104 and being connected by a ball and socket joint 94 to a connecting rod or link 105 as in the first embodiment.

The distal section comprises a housing 106 dependent from and pivotally connected to the distal end of proximal section 101a for angular adjustment about a transverse axis, an outwardly convex flexible cylindrical wall 107a extending between the proximate outer ends of the proximal and distal housings to permit such angular adjustment.

Mounted in distal housing 106 along the end side wall thereof is an open ended bearing sleeve 107 locked against axial and angular movement by a set screw 108, the ends of sleeve 107 registering with opposing end openings in housing 106. A tubular piston assembly 109 is coaxially reciprocatable in sleeve 107 and has an axial bore 96 tapering outwardly at its distal end and being tapped at its inner end and engaging a mating longitudinally slit collet 110 which functions to hold a tool coupling shank and is axially adjustable to effect its tightening and loosening. A longitudinal slot 115a is formed in the inner portion of the wall of sleeve 107 and a longitudinal rack 112 is formed on the upper side of reciprocatable ram or piston 111. The piston 111 is prevented from rotating about its longitudinal axis by a radial projection 115 on piston 111 slideably engaging a longitudinal groove 115a in the inside face of sleeve 107. Projection 115 also projects upward, engaging a slot in collet 110 to prevent collet 110 from rotating about its longitudinal axis. Piston 109 is free to rotate about its axis and when rotated by means of suitable tool engaging a mating opening 117 will by means of mating threaded sections be able to draw the collet into the tapered opening of 111 causing it to grip tools intended to be used with the instrument 100. Rotating piston 109 in the opposite direction will release collet 110 allowing tools to be removed.

Mounted by a pivot member 113 in housing 106 above rack 112 and forward of actuator member 104 for rocking about a transverse axis is sector gear member 114. Gear member 114 engages rack 112 and is provided with an oppositely projecting arm 97 and is rockable about a transverse axis at the inner end of arm 97, the outer end of gear member arm 97 remote from the rack 112 is connected by a ball and socket joint 98 to the link 105. The link 105 consists of a pair of opposite ball sections having radially projecting shanks joined by a coupling sleeve 99.

The operation and application of the modified device 100 are similar to those of the device 10 described earlier. Rotation of the shaft 103 reciprocates the piston assembly by way of actuator member 104, link 105, gear sector 114 and rack 112 and angular adjustment between the proximal and distal sections 101 and 102 does not significantly effect the stroke length of piston assembly 109.

While there have been described and illustrated preferred embodiments of the present invention, it is apparent that numerous alterations, omissions and additions may be made without departing from the spirit thereof.

We claim:

1. A dental handpiece attachment comprising an articulated member including a pair of relatively angularly adjustable proximal and distal housing sections, a longitudinally extending shaft rotatably supported in said proximal section and restricted against axial movement, a slide member longitudinally reciprocatably supported in said distal section and restricted against rotation, means for attaching a tool to the distal portion of said slide member and a rotation to reciprocation motion translator in proximal section transmitting said translation to distal member by means of a link coupling said shaft to said slide member and effective to reciprocate said slide member with rotation of said shaft substantially independently of the relative angular relationship between said tubular sections for at least a predetermined range of said angular adjustment.

2. The dental handpiece attachment of claim 1 wherein said predetermined range is between angular adjustments wherein the axes of said drive shaft and slide member are parallel and perpendicular to each other.

3. The dental handpiece attachment of claim 1 including means for releasably locking said tubular sections at preselected angular adjustments thereof.

4. The dental handpiece attachment of claim 1 wherein said motion translator includes an actuator member rockably supported between said shaft and slide member and restricted against rotation about the axis of said shaft, a coupling pin projecting forwardly from the front end of, at an angle to the longitudinal axis of said shaft and rotatable with said shaft and journalled to said actuator member whereby to rock said actuator member with the rotation of said shaft and coupling means including a link coupling said actuator member and slide member.

5. The dental handpiece attachment of claim 4 wherein said actuator member includes a transversely extending first section having a bore engaging said coupling pin and a longitudinally extending second section engaged by one end of said link.

6. The dental handpiece attachment of claim 5 wherein said actuator member first section has a longitudinal groove formed in an outer face thereof and including a pin mounted on said body member distal section and slideably engaging said groove.

7. The dental handpiece attachment of claim 5 wherein said link comprises a rod having spherical elements at opposite ends thereof, and the proximate ends of said slide member and actuator member second sections have spherical sockets universally rockably engaged by the respective spherical elements on said rod.

8. The dental handpiece attachment of claim 7 including a spring resiliently rearwardly urging said slide member.

9. The dental handpiece attachment of claim 1 wherein said tool attaching means comprises a chuck mounted on the forward portion of said slide member forwardly of said body member distal section and adapted to releasably engage a replaceable tool.

10. A dental handpiece attachment comprising an articulated member including a pair of relatively angularly adjustable proximal and distal housing sections, a longitudinally extending shaft rotatably supported in said proximal section and restricted against axial movement, a slide member longitudinally reciprocatably supported in said distal section and restricted against rotation, means for attaching a tool to the distal portion of said slide member and a rotation to reciprocation motion translator coupling said shaft to said slide member and effective to reciprocate said slide member with rotation of said shaft substantially independently of the relative angular relationship between said tubular sections for at least a predetermined range of said angular adjustment.

11. The dental handpiece attachment of claim 10 wherein said motion translator includes an actuator member rockably supported between said shaft and slide member and restricted against rotation about the axis of said shaft, a coupling pin projecting forwardly from the front end of, at an angle to the longitudinal axis of said shaft and rotatable with said shaft and journalled to said actuator member whereby to rock said actuator member with the rotation of said shaft and coupling means including a link coupling said actuator member and slide member.

12. The dental handpiece attachment of claim 11 wherein said coupling means includes a rack coupled to and slideable with said slide member and a gear member rockable about a transverse axis and engaging said rack, one end of said link being coupled to said gear member at a point eccentric to said transverse axis.

13. The dental handpiece attachment of claim 10 wherein said slide member comprises a tubular piston and said tool attaching means comprises a collet member telescoping said tubular piston.

14. The dental handpiece attachment of claim 13 wherein said tubular piston has a tapped axial bore flaring at its front end and said collet member is externally threaded and engages said tapped bore end includes an outwardly flared longitudinally split contractable front end registering with the flared end of said piston bore.

* * * * *